(12) United States Patent
McGovern et al.

(10) Patent No.: US 6,554,838 B2
(45) Date of Patent: Apr. 29, 2003

(54) METHOD AND APPARATUS FOR IMPLANTING A PROSTHETIC DEVICE

(75) Inventors: Michael J. McGovern, Mahwah, NJ (US); Anthony O'Hehir, Wharton, NJ (US); Louie Serpe, Monroe, NY (US); Imants Liepins, Hoboken, NJ (US)

(73) Assignee: Howmedica Osteonics Corp., Allendale, NJ (US)

( * ) Notice: Subject to any disclaimer, the term of this patent is extended or adjusted under 35 U.S.C. 154(b) by 0 days.

(21) Appl. No.: 09/871,153

(22) Filed: May 31, 2001

(65) Prior Publication Data

US 2002/0183760 A1 Dec. 5, 2002

(51) Int. Cl.[7] .................................................. A61F 5/00
(52) U.S. Cl. ........................................................ 606/87
(58) Field of Search ................................ 606/79, 80, 87, 606/88, 89

(56) References Cited

U.S. PATENT DOCUMENTS

| | | | |
|---|---|---|---|
| 4,719,008 A | | 1/1988 | Averill et al. |
| 4,892,093 A | * | 1/1990 | Zarnowski et al. ........... 606/82 |
| 5,108,400 A | * | 4/1992 | Appel et al. .................. 606/79 |
| 5,474,559 A | | 12/1995 | Bertin et al. |
| 5,486,180 A | | 1/1996 | Dietz et al. |
| 5,520,695 A | * | 5/1996 | Luckman ...................... 606/88 |
| 5,653,714 A | * | 8/1997 | Dietz et al. ................... 606/87 |
| 5,709,689 A | * | 1/1998 | Ferrante et al. ............... 606/86 |
| 6,056,754 A | * | 5/2000 | Haines et al. ................. 606/80 |

OTHER PUBLICATIONS

Biomet Merck Limited, Genus Uni Knee System Technique, Surgical Technique by Jonathan Braslow, M.D., undated.
Bjorn E.J. Albrektsson, M.D., Ph.D., et al, The MIS Minimally Invasive Solution from Zimmer Combines a Minimally Invasive Technique with Precise Instrumentation, undated.

* cited by examiner

Primary Examiner—Eduardo C. Robert
(74) Attorney, Agent, or Firm—Arthur Jacob

(57) ABSTRACT

Method and apparatus for preparing a seating surface of prescribed depth, contour configuration and area delineated by a prescribed peripheral boundary extending along the bone of a natural joint at which a prosthetic device is to be implanted includes positioning a guide on the bone, the guide having a guide slot following a path geometrically similar to the peripheral boundary of the seating surface, inserting a cutting device altitudinally through the guide slot at any selected location along the path of the guide slot, and translating the cutting device along the guide slot to cut an outline groove in the bone coincident with the peripheral boundary of the seating surface. The guide then is removed from the bone, and portions of the bone lying within the area delineated by the outline groove are removed to establish the seating surface.

24 Claims, 7 Drawing Sheets

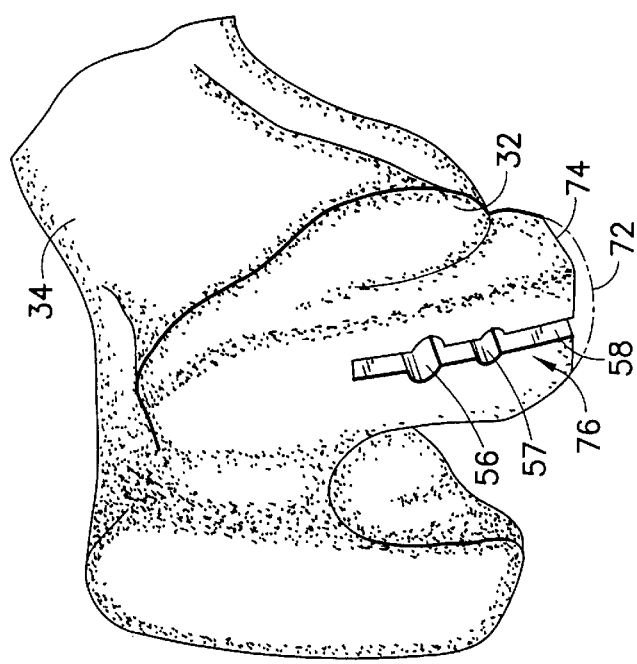
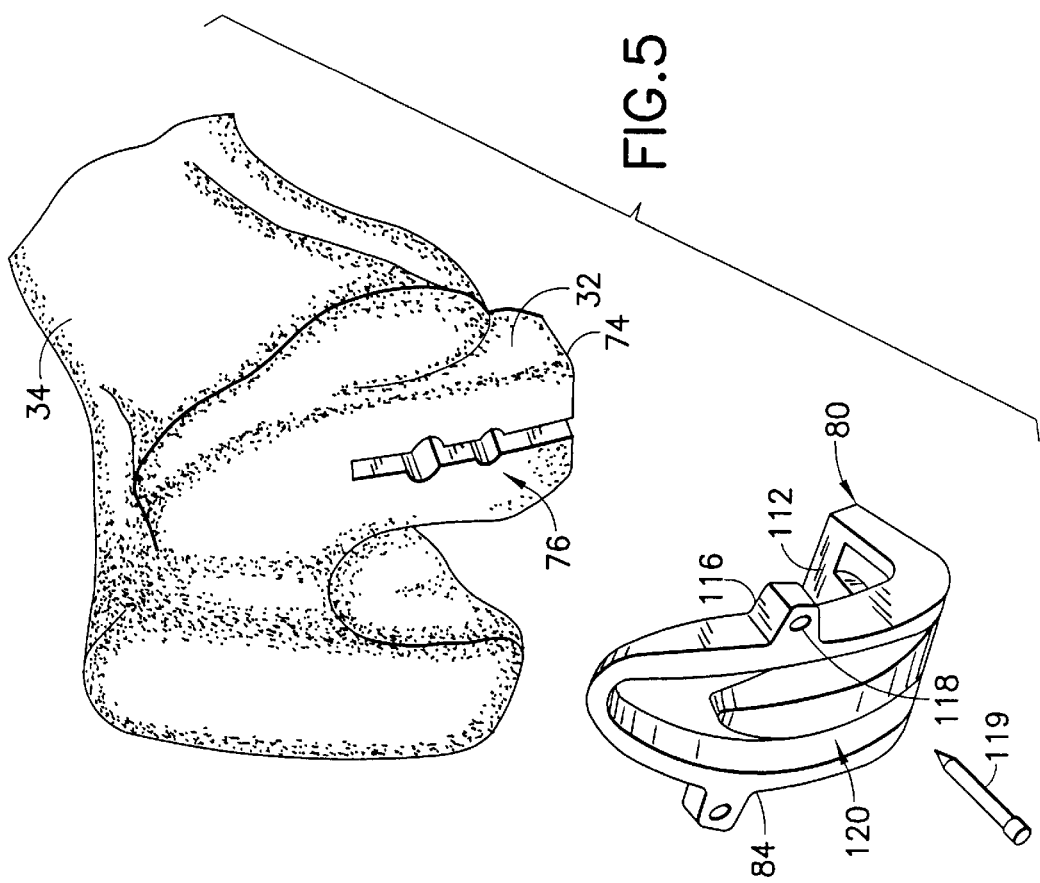

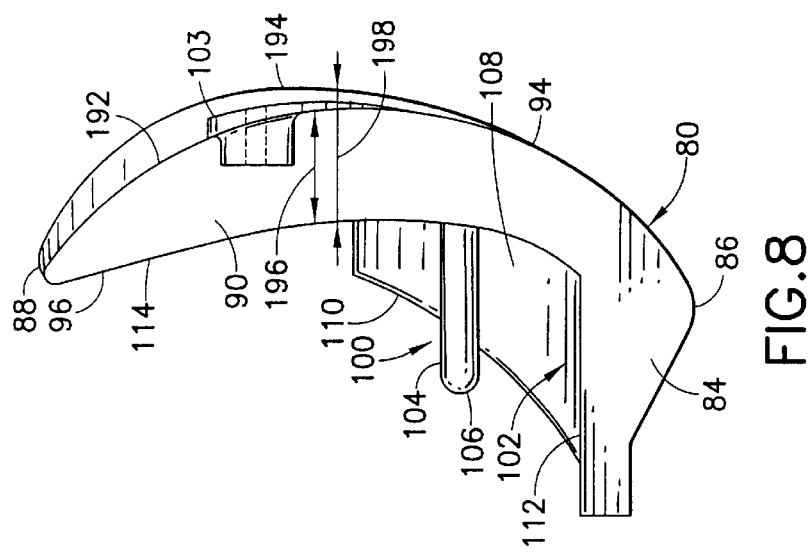
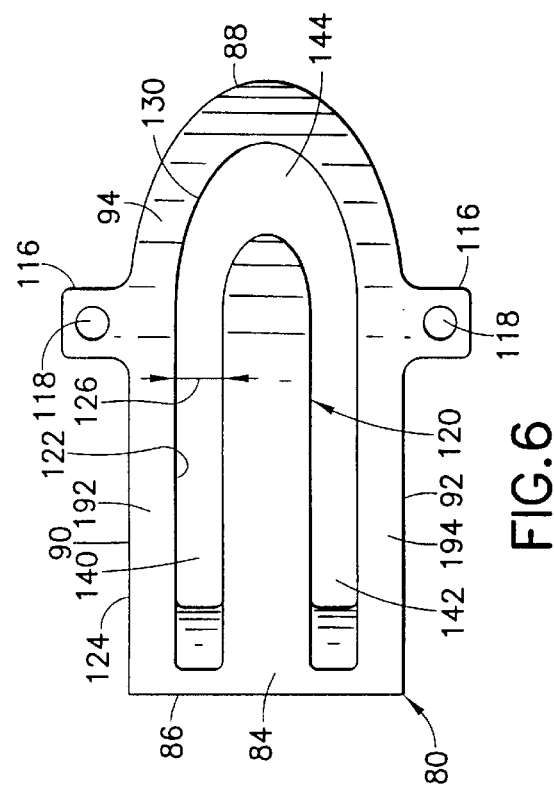
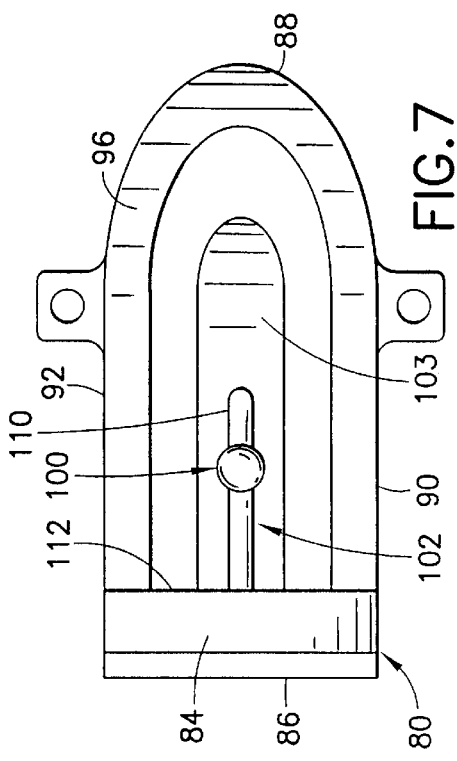

METHOD AND APPARATUS FOR IMPLANTING A PROSTHETIC DEVICE

The present invention relates generally to the implant of prosthetic devices at various joints in the body and pertains, more specifically, to method and apparatus for preparing the bone at the joint for receiving a component part or parts of the prosthetic device to be implanted.

The use of prosthetic devices to replace damaged natural joints, or portions of such joints, in the body has become widespread as medical and technological advances have joined to provide improved materials and configurations for prosthetic devices and innovative procedures for implanting these devices. The basic objective of such devices and procedures, of course, is to provide a repaired joint of maximum effectiveness, with a minimal intrusion into the body of the recipient of the device. Component parts of the prosthetic device are utilized to replace portions of a natural joint which have become damaged, either through injury or disease, and it is usually necessary to remove portions of the natural joint beyond merely the damaged portions in order to enable stable and secure affixation of the component parts to the natural bone. In addition, access to damaged joints is limited and the necessity for reaching the areas to be worked upon can affect the extent of intrusion required to complete an effective implant.

Among the objects and advantages of the present invention in providing an improved method and apparatus by which a prosthetic device may be implanted at the joint of a body are those which are summarized as follows: Requires removal of only a minimal amount of the natural bone at the joint, consistent with enabling stable and secure affixation of each component part of the prosthetic device; attains accuracy in the delineation of the area, depth and contour configuration of the prepared surfaces of the bone which will receive a component part of the prosthetic implant; enables such accuracy within the confines of the limited access available at the joint, with minimal disturbance of surrounding tissue in the vicinity of the joint; allows the use of a minimum number of instruments and steps of limited complexity in carrying out the procedure; provides the ability to use currently available instruments in connection with elements of the present apparatus and current techniques in connection with the steps of the present method for compatibility and widespread acceptance among surgeons; allows a certain amount of discretion on the part of the surgeon in accommodating particular conditions encountered at an implant site, while preserving ease and accuracy in completing preparation of the site for the implant.

The above objects and advantages, as well as further objects and advantages, are attained by the present invention which may be described briefly as apparatus for preparing a seating surface of prescribed depth, contour configuration and area delineated by a prescribed peripheral boundary extending along the bone of a natural joint at which a prosthetic device is to be implanted, the bone having been provided with at least a partially prepared site for locating and seating a component part of the prosthetic device at the seating surface, the apparatus comprising: a depth, contouring and area guide block having longitudinally opposite first and second ends, laterally opposite first and second sides, an upper locator surface and a lower guide locating surface; at least a portion of the upper locator surface having a profile contour configuration essentially matching a corresponding portion of the contour configuration of the seating surface; a holding arrangement integral with the guide block for holding the guide block on the bone at the site with the guide block placed at a predetermined location and orientation relative to the bone; a guide slot passing altitudinally through the guide block from the upper locator surface to the lower guide locating surface, the guide slot having a length, a laterally outer locator edge extending along a path geometrically similar to the peripheral boundary of the seating surface, a laterally inner edge and a lateral width between the outer locator edge and the inner edge; and a cutting device for reception within the guide slot, the cutting device having a cutting axis for extending altitudinally when the cutting device is received within the guide slot, an axial cutting surface for rotation about the cutting axis, the axial cutting surface having a near end and a far end, a radial cutting surface transverse to the axial cutting surface at the far end, a radial bearing surface located at a predetermined axial distance from the radial cutting surface, and an axial bearing surface located axially between the radial bearing surface and the near end of the axial cutting surface; the axial cutting surface having a diameter less than the lateral width of the guide slot, the axial bearing surface having a diameter less than the lateral width of the guide slot, and the radial bearing surface having a diameter greater than the lateral width of the guide slot, the diameters of the axial cutting surface, the axial bearing surface and the radial bearing surface having relative dimensions such that upon reception of the cutting device within the guide slot, the cutting device is capable of insertion axially into the guide slot in an altitudinal direction at any selected location along the length of the guide slot, the axial bearing surface follows the contour configuration of the outer locator edge of the guide slot to locate the axial cutting surface along the peripheral boundary of the seating surface while the radial bearing surface follows the upper locator surface, with the radial bearing surface overlying the outer locator edge and the inner edge of the guide slot to stabilize and locate the radial cutting surface at the prescribed depth of the seating surface.

The invention further includes an improvement in an apparatus for preparing a seating surface of prescribed depth, contour and area placed within a prescribed peripheral boundary extending along the bone of a natural joint at which a prosthetic device is to be implanted, the bone having been provided with at least a partially prepared site for locating and seating a component part of the prosthetic device at the seating surface, the apparatus including a depth, contouring and area guide for guiding a cutting device to be received within the guide, the cutting device having a cutting axis for extending altitudinally within the guide, an axial cutting surface for rotation about the cutting axis, the axial cutting surface having a first diameter, a near end and a far end, a radial cutting surface transverse to the axial cutting surface at the far end, a radial bearing surface having a second diameter and being located at a predetermined axial distance from the radial cutting surface, and an axial bearing surface having a third diameter and being located axially between the radial bearing surface and the near end of the axial cutting surface, the improvement comprising: a depth, contouring and area guide block having longitudinally opposite first and second ends, laterally opposite first and second sides, an upper locator surface and a lower guide locating surface; at least a portion of the upper locator surface having a profile contour configuration essentially matching a corresponding portion of the contour configuration of the seating surface; a holding arrangement integral with the guide block for holding the guide block on the bone at the site with the guide block placed at a predetermined location and orientation relative to the bone; and a guide slot extending altitudinally through the guide block from the upper locator surface to the lower guide locating surface, the guide slot having a length, a laterally outer locator edge following a path geometrically similar to the peripheral boundary of the seating surface, a laterally inner edge and a lateral width between the outer locator edge and the inner edge; the lateral width of the guide slot being greater than each of the first and third diameters and less than the second diameter with the first, second and third diameters having relative dimensions such that upon reception of the cutting device within the guide slot, the cutting device is capable of insertion axially into the guide slot in an altitudinal direction at any selected location along the length of the guide slot, the axial bearing surface follows the outer locator edge of the guide slot to locate the axial cutting surface along the peripheral boundary of the seating surface while the radial bearing surface follows the upper locator surface, with the radial bearing surface overlying the outer locator edge and the inner edge of the guide slot to stabilize and locate the radial cutting surface at the prescribed depth of the seating surface.

Still further, the invention includes an improvement in an apparatus for preparing a seating surface of prescribed depth, contour and area delineated by a prescribed peripheral boundary extending along the bone of a natural joint at which a prosthetic device is to be implanted, the bone having been provided with at least a partially prepared site for locating and seating a component part of the prosthetic device at the seating surface, the apparatus including a depth, contouring and area guide block having longitudinally opposite first and second ends, laterally opposite first and second sides, an upper locator surface and a lower guide locating surface, at least a portion of the upper locator surface having a profile contour configuration essentially matching a corresponding portion of the contour configuration of the seating surface, a holding arrangement integral with the guide block for holding the guide block on the bone at the site with the guide block placed at a predetermined location and orientation relative to the bone, a guide slot extending altitudinally through the guide block from the upper locator surface to the lower guide locating surface, the guide slot having a length, a laterally outer locator edge following a path geometrically similar to the peripheral boundary of the seating surface, a laterally inner edge and a lateral width between the outer locator edge and the inner edge, the improvement comprising: a cutting device for reception within the guide slot, the cutting device including a cutting axis for extending altitudinally when the cutting device is received within the guide slot; an axial cutting surface for rotation about the cutting axis, the axial cutting surface having a near end and a far end; a radial cutting surface transverse to the axial cutting surface at the far end; a radial bearing surface located at a predetermined axial distance from the radial cutting surface; and an axial bearing surface located axially between the radial bearing surface and the near end of the axial cutting surface; the axial cutting surface having a diameter less than the lateral width of the guide slot, the axial bearing surface having a diameter less than the lateral width of the guide slot, and the radial bearing surface having a diameter greater than the lateral width of the guide slot, the diameters of the axial cutting surface, the axial bearing surface and the radial bearing surface having relative dimensions such that upon reception of the cutting device within the guide slot, the cutting device is capable of insertion axially into the guide slot in an altitudinal direction at any selected location along the length of the guide slot, the axial bearing surface follows the outer locator edge of the guide slot to locate the axial cutting surface along the peripheral boundary of the seating surface while the radial bearing surface follows the upper locator surface, with the radial bearing surface overlying the outer locator edge and the inner edge of the guide slot to stabilize and locate the radial cutting surface at the prescribed depth of the seating surface.

In addition, the invention includes a method of preparing a seating surface of prescribed depth, contour and area delineated by a prescribed peripheral boundary extending along the bone of a natural joint at which a prosthetic device is to be implanted, the bone having been provided with at least a partially prepared site for locating and seating a component part of the prosthetic device at the seating surface, the method comprising the steps of: positioning a depth, contouring and area guide on the bone at the site, the guide including a guide slot having a length following a path geometrically similar to the peripheral boundary of the seating surface, the length including longitudinal length portions spaced apart laterally; engaging a cutting device with the guide by inserting the cutting device altitudinally through the guide slot at any selected location along the path of the guide slot; translating the cutting device along the length of the guide slot to cut an outline groove in the bone coincident with the peripheral boundary of the seating surface such that the outline groove establishes an outline contiguous with the area of the seating surface; removing the guide from the bone subsequent to translating the cutting device along the length of the guide slot; and removing portions of the bone lying within the area contiguous with and delineated by the outline groove to establish the seating surface.

The invention will be understood more fully, while still further objects and advantages will become apparent, in the following detailed description of preferred embodiments of the invention illustrated in the accompanying drawing, in which:

FIG. 4 is a fragmentary perspective view showing the femoral condyles with the medial side compartment partially prepared to receive the femoral component;

FIG. 5 is a fragmentary perspective view showing a depth, contouring and area guide constructed in accordance with the present invention about to be installed on the partially prepared condyle;

FIG. 6 is a top plan view of the depth, contouring and area guide;

FIG. 7 is a bottom plan view of the depth, contouring and area guide;

FIG. 8 is a side elevational view of the depth, contouring and area guide;

Figure 1:
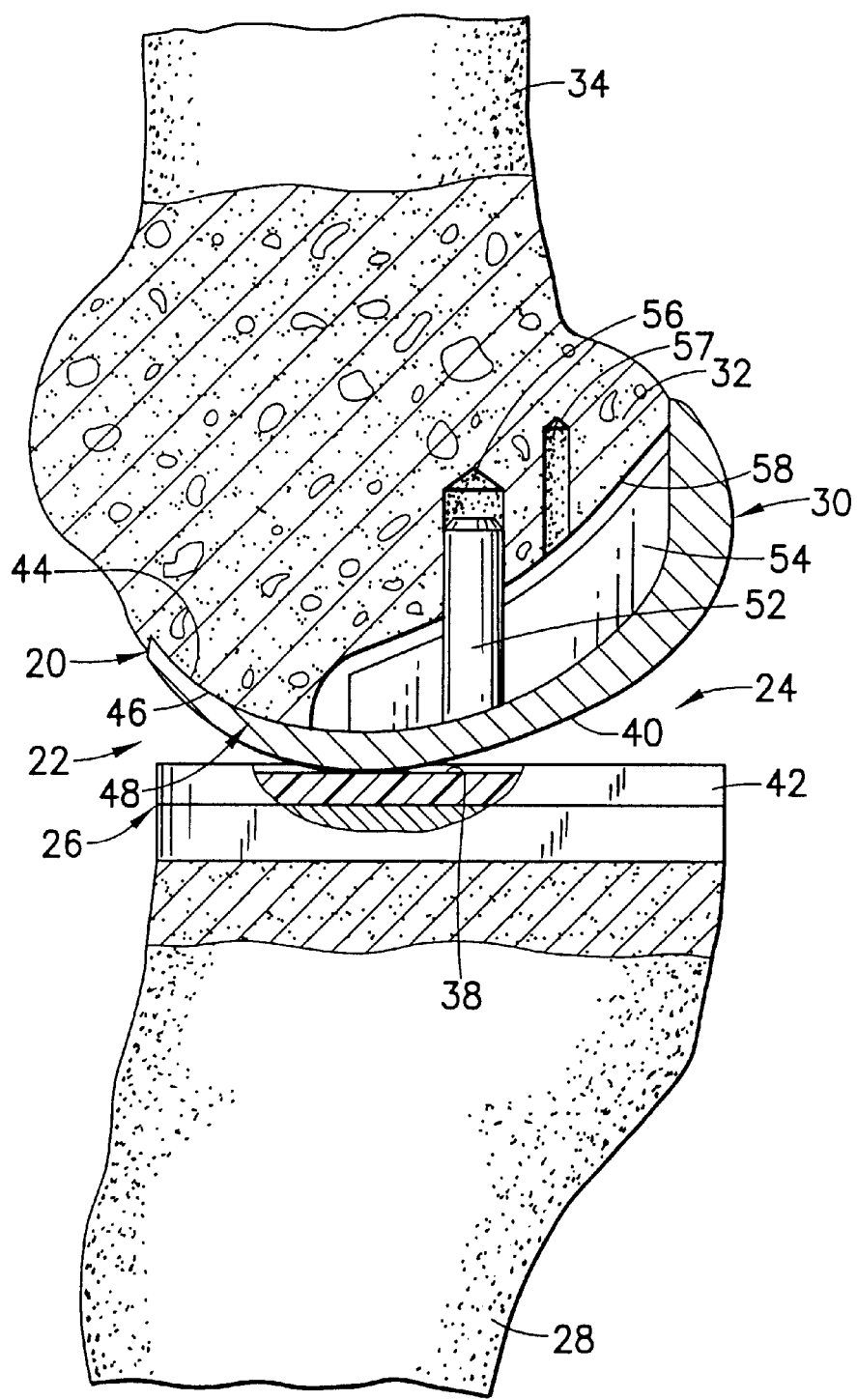
FIG. 1 is a pictorial view, partially cross-sectioned, of a body joint in the form of a knee joint within which a prosthetic device has been implanted.
Figure 2:
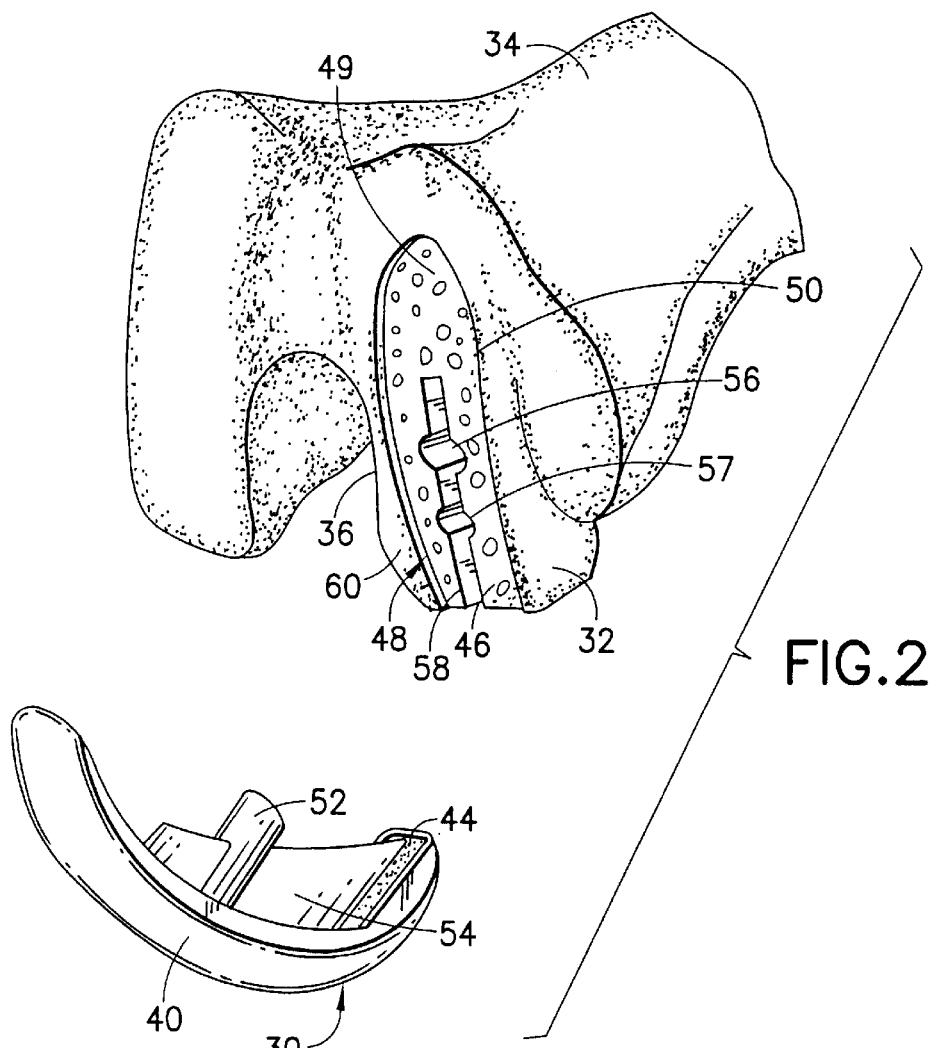
FIG. 2 is a fragmentary perspective view showing the femoral component of the prosthetic device about to be affixed to a femoral condyle.

Referring now to the drawing, and especially to FIGS. 1 and 2 thereof, a prosthetic device is illustrated in the form of a unicompartmental knee prosthesis 20 implanted in the medial side compartment 22 of a knee joint 24. Knee prosthesis 20 includes a tibial component 26 affixed to the tibia 28 and a unicondylar femoral component 30 affixed to the femoral condyle .32 of the medial side compartment 22 of the femur 34, adjacent trochlear groove 36. The tibial component 26 provides an articular surface 38 upon which the outer surface 40 of the femoral component 30 moves during articulation of the knee joint 24.

Tibial component 26 includes a tibial pad 42 constructed of a synthetic polymeric material, such as a high-density polyethylene, which provides the articular surface 38 with the appropriate lubricity characteristics for proper functioning of the prosthesis 20. Femoral component 30 preferably is constructed of a metallic material compatible with its use within the body. The arcuate outer surface 40 replaces the damaged natural bone of the femoral condyle 32 and follows, as closely as is practicable, the contour of the replaced bone.

It is desirable to fit the femoral component 30 accurately to the condyle 32 so that the inner surface 44 of the femoral component 30 is registered and contiguous with a seating surface 46 on the condyle 32, at prepared site 48. In this manner, only minimal bone is removed, enabling the femoral component 30 to be seated upon a superior foundation provided by the relatively dense, stronger bone available nearer the outer surface of the condyle 32, and by the geometric contour of the seating surface 46. In addition, the intimate contact attained between the inner surface 44 of the femoral component 30 and the seating surface 46 enhances fixation, either with or without the use of adhesive. At the same time, proper fitting of the femoral component 30 to the condyle 32, including proper registration for appropriate location and orientation, requires the accurate formation of the area 49 of the seating surface 46, as delineated by a prescribed peripheral boundary 50 extending along the bone, around the seating surface 46, as well as the accurate formation of the prescribed depth and contour of the seating surface 46 throughout the area 49. Femoral component 30 incorporates a fixation arrangement in the form of a fixation peg 52 projecting from the inner surface 44 and a fixation keel 54, also projecting from the inner surface 44, for reception of the peg 52 in complementary hole 56 and reception of the keel 54 in complementary slot 58 of prepared site 48 at the surface 60 of the bone of condyle 32 to locate the femoral component 30 in appropriate registration on the condyle 32 and hold the femoral component 30 registered at that location.

In FIG. 2, the femoral component 30 is about to be implanted on the condyle 32. The condyle 32 has been prepared in accordance with the present invention, as will be described more fully below, so that the seating surface 46 is ready to receive the inner surface 44 of the femoral component 30 in the desired contiguous mating relationship, with the femoral component 30 appropriately registered on condyle 32.

Figure 3:
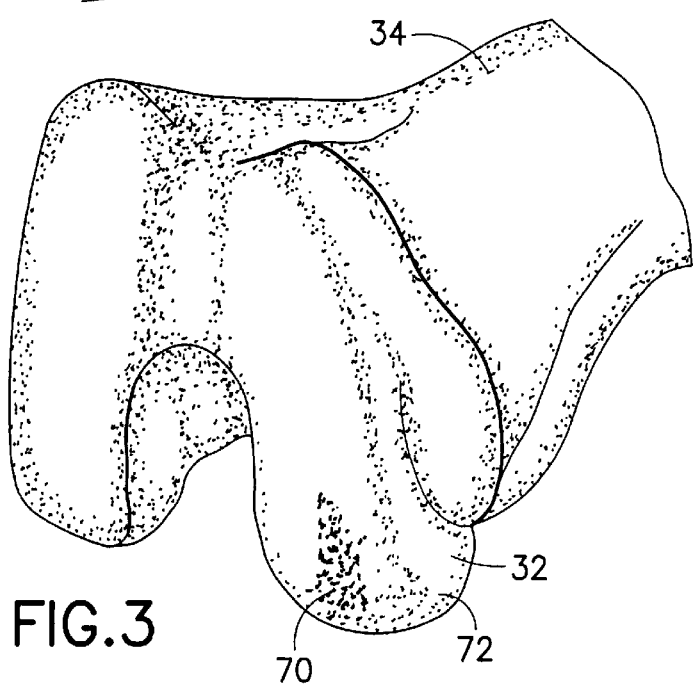
FIG. 3 is a fragmentary perspective view showing the femoral condyles prior to one condyle being prepared for the implant of a prosthetic device.

Turning now to FIG. 3, the femur 34 is shown prior to the preparation of femoral condyle 32 for the implant of femoral component 30. Damaged bone 70 of condyle 32 is to be removed and the femoral component 30 is to be implanted to replace the function of the damaged bone 70 in the knee joint 24.

In FIG. 4, condyle 32 has been prepared partially by drilling hole 56, then drilling hole 57, then cutting off a portion 72 of the condyle 32 to establish a flat posterior surface 74 on the condyle 32, and then cutting slot 58 to construct a partially prepared site 76 on condyle 32. The drilling of holes 56 and 57, the cutting to establish posterior surface 74, and the cutting of slot 58, are conventional in current implant procedures, and fixtures are available for assuring that the holes 56 and 57, the posterior surface 74, and the slot 58 are located accurately on the condyle 32.

Referring now to FIG. 5, a depth, contouring and area guide constructed in accordance with the present invention is shown at 80 and is about to be installed at the partially prepared site 76 on condyle 32 for assisting in the further preparation of the condyle 32 to receive femoral component 30 at the fully prepared site 48. As best seen in FIGS. 6, 7 and 8, as well as in FIG. 5, guide 80 includes a guide block 84 having longitudinally opposite first and second ends 86 and 88, respectively, laterally opposite first and second sides 90 and 92, respectively, an upper locator surface 94 and an altitudinally lower guide locating surface 96. The lower guide locating surface 96 has a contour configuration which includes a curvilinear profile contour extending from the first end 86 toward the second end 88 to match, essentially, the profile contour of the bone at site 76 on condyle 32 so as to attain a firm and stable seating of the guide block 84 on the condyle 32.

A holding arrangement is integral with the guide block 84 for holding the guide block 84 at the partially prepared site 76 on the condyle 32, at a predetermined location and orientation relative to the bone at the site 76. Holding arrangement is shown in the form of a post 100 and a fin 102, both placed laterally between the opposite sides 90 and 92 of the guide block 84, on a generally central portion 103 of the guide block 84, and projecting altitudinally downwardly from the lower guide locating surface 96, essentially normal to the lower guide locating surface 96. Post 100 includes a generally cylindrical pin portion 104 terminating at a rounded terminal end 106. Fin 102 is integrated with post 100 and includes a wall portion 108 essentially coextensive with post 100 and terminating at a rounded edge 110. Pin portion 104 has a diameter slightly less than the diameter of hole 57, and wall portion 108 has a wall thickness slightly less than the width of slot 58 so that the relative dimensions of pin portion 104 and hole 57, and the relative dimensions of wall portion 108 and slot 58 enables insertion of the pin portion 104 into hole 57, and insertion of wall portion 104 into slot 58 for locating guide block 84 relative to hole 57 and slot 58 and holding guide block 84 in place on condyle 32, the insertion being facilitated by the rounded terminal end 106 and the rounded terminal edge 110. The fit between post 100 and hole 57, and between fin 102 and slot 58, assures accurate registration of the guide block 84 in an appropriate location and orientation relative to the bone of condyle 32, and stable holding of the guide block 84 on the bone in such registration.

Registration and stability of the guide block 84 at the partially prepared site 76 is enhanced by an essentially planar surface portion 112 of the lower guide locating surface 96 extending in an altitudinal direction, downwardly from curved portion 114 of the lower guide locating surface 96, adjacent the first end 86 of the guide block 84. Planar surface portion 112 engages posterior surface 74 of condyle 32 for such enhanced registration and stability. Should it be desired to secure guide block 84 to the bone of condyle 32 in a more positive fashion, an ear 116 is provided at each side 90 and 92, each ear 116 including an aperture 118 for optional reception of a securing pin 119 to be driven into the bone to anchor the guide block 84 in place.

Guide block 84 includes a guide slot 120 passing altitudinally through the guide block 84 from the upper locator surface 94 to the lower guide locating surface 96. Guide slot 120 has a laterally outer locator edge 122, a laterally inner edge 124, and a lateral width 126 between the laterally spaced apart outer locator edge 122 and inner edge 124. Outer locator edge 122 extends along a path 130 which is geometrically similar to the peripheral boundary 50 of the seating surface 46; that is, path 130 has the same geometric shape as peripheral boundary 50, but not necessarily the same dimensions. In the present embodiment, for purposes to be described below, path 130 follows a perimeter greater than. that of peripheral boundary 50 and lies outside area 49 of seating surface 46, when guide block 84 is in place on condyle 32, with path 130 spaced laterally from peripheral boundary 50. Consequently, guide slot 120 generally follows the outline configuration of seating surface 46 and includes a first leg 140 extending longitudinally from the first end 86 of the guide block 84 toward the second end 88, adjacent the first side 90 of guide block 84, a second leg 142 extending longitudinally from the first end 86 toward the second end 88, adjacent the second side 92 of guide block 84, and a third leg 144 extending laterally from the first leg 140 to the second leg 142, adjacent the second end 88 of the guide block 84, all providing guide slot 120 with a generally U-shaped configuration.

Figure 9:
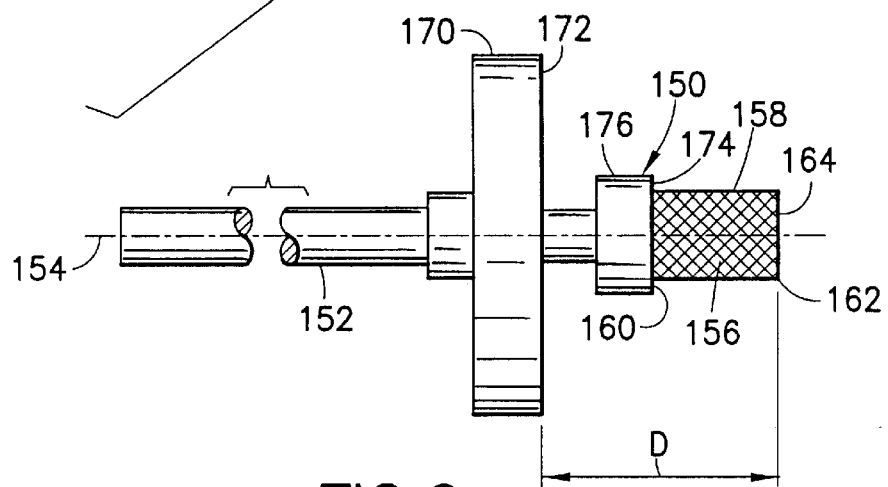
FIG. 9 is an elevational view of a cutting device constructed in accordance with the present invention.

Turning now to FIG. 9, a cutting device constructed in accordance with the invention is illustrated in the form of a burr assembly 150 having a central shaft 152 extending along a cutting axis 154. A cutter in the form of a burr 156 is mounted upon shaft 152 for rotation with the shaft 152 about axis 154 and includes a generally cylindrical axial cutting surface 158 extending axially between a near end 160 and a far end 162. A radial cutting surface 164 on the burr 156 extends transverse to the cutting axis 154 at the far end 162. A radial bearing member 170 is journaled for rotation on central shaft 152, adjacent the near end 160, and includes a radial bearing surface 172 spaced a predetermined axial distance D from the radial cutting surface 164, and the far end 162. An axial bearing member 174 is journaled for rotation on shaft 152 and includes a generally cylindrical axial bearing surface 176 located axially between the radial bearing surface 172 and the near end 160 of the axial cutting surface 158. In the illustrated embodiment, axial bearing surface 176 has a diameter less than the lateral width 126 of guide slot 120, axial cutting surface 158 has a diameter less than the diameter of the axial bearing surface 176 and, consequently, less than the width 126 of guide slot 120, and the radial bearing surface 172 has a diameter greater than the width 126 of guide slot 120, for purposes to be described below.

Figure 10:
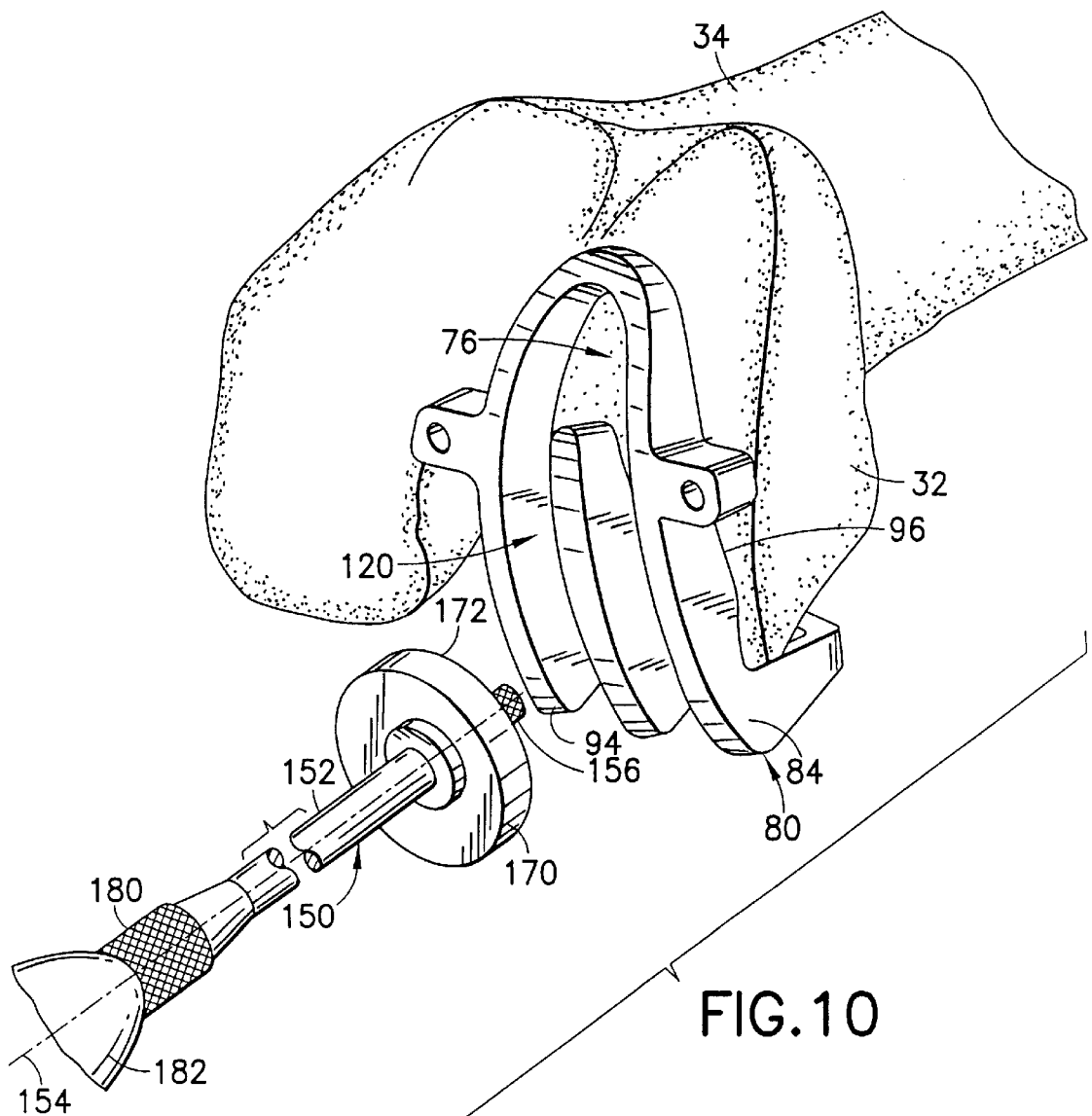
FIG. 10 is an enlarged fragmentary perspective view showing the depth, contouring and area guide installed on the partially prepared condyle and about to be engaged by the cutting device.

In FIG. 10, guide block 84 is shown installed on condyle 32. Guide block 84 has been urged toward condyle 32, as by light tapping, until the lower guide locating surface 96 is seated against the subchondral bone of the condyle 32. Hole 57 and slot 58 are deep enough so that the terminal end 106 of post 100 and the terminal edge 110 of fin 102 are spaced away from the bottom of the hole 57 and the bottom of the slot 58 to assure proper seating of the guide block 84 at the partially prepared site 76 on condyle 32.

Figure 11:
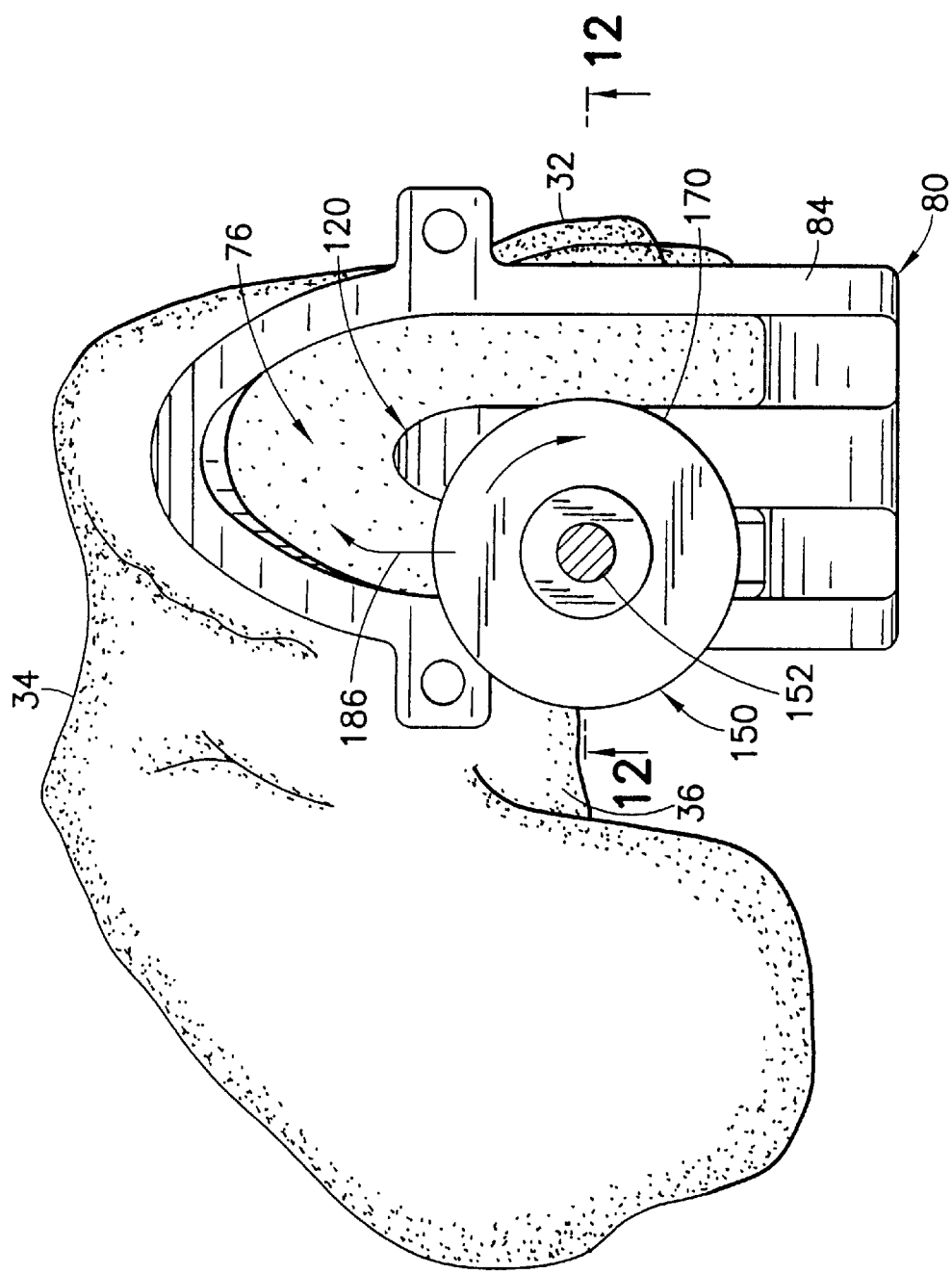
FIG. 11 is a pictorial view showing the cutting device engaged with the installed depth, contouring and area guide during performance of the method of the present invention.
Figure 12:
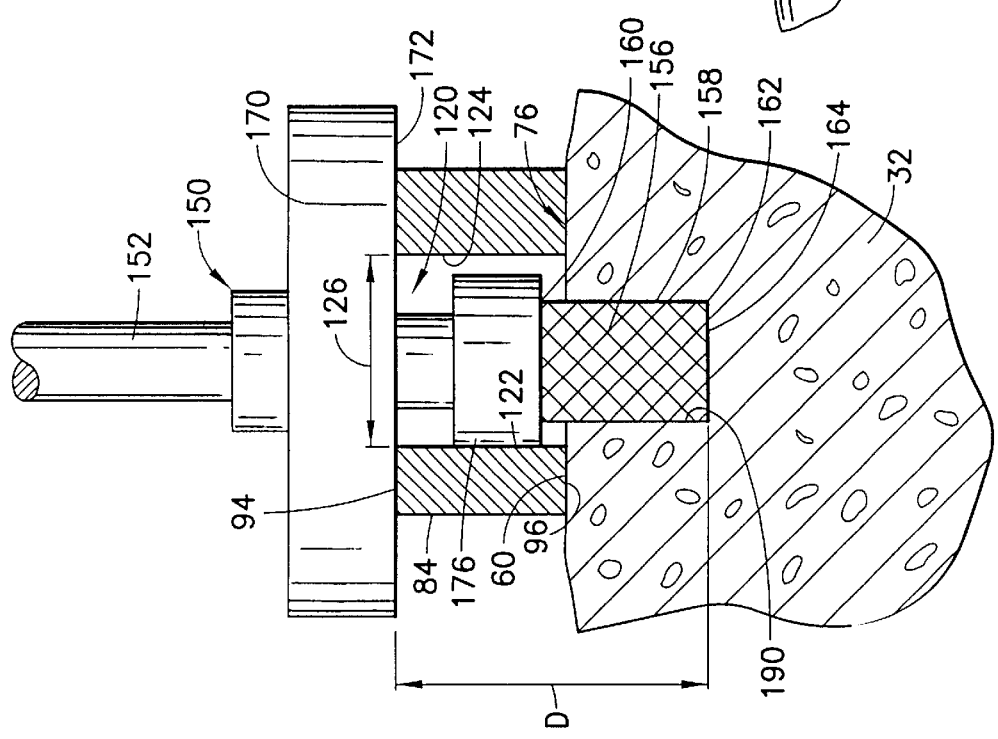
FIG. 12 is an enlarged, fragmentary cross-sectional view taken along line 12—12 of FIG. 11.

As seen in FIGS. 10 through 12, burr assembly 150 is affixed to a chuck 180 of a power-operated tool 182 for rotation of the burr assembly 150 and, with the guide block 84 installed as described above, burr assembly 150 is inserted into guide slot 120 of guide block 84, with the cutting axis 154 of shaft 152 aligned generally with an altitudinal direction. The relative dimensions of the diameters of the axial cutting surface 158, the axial bearing surface 176 and the radial bearing surface 172 are such that upon altitudinal movement of the burr assembly 150 into the guide slot 120 the radial bearing surface 172 engages the upper locator surface 94 at both the laterally outer locator edge 122 and the laterally inner edge 124 of the guide slot 120, as illustrated in greater detail in FIG. 12, and burr 156 will enter the bone of condyle 32 up to a depth determined by the elevation of the upper locator surface 94 above the surface 60 of the bone of condyle 32 and the predetermined distance D between the radial bearing surface 172 and radial cutting surface 164 at the far end 162.

Upon longitudinal translation of the burr assembly 150 along the guide slot 120, as indicated by arrow 186 in FIG. 11, with the axial bearing surface 176 maintained against the laterally outer locator edge 122, the cutting surfaces 158 and 164 will remove bone to cut an outline groove 190 in the bone, as seen in FIG. 12. As a result of the relative dimensions of the diameters of the axial bearing surface 176 and the axial cutting surface 158, outline groove 190 is coincident with the peripheral boundary 50 of the seating surface 46 so that the outline groove 190 delineates accurately the area 49 of the seating surface 46. As the burr assembly 150 is translated along the guide slot 120, with the radial bearing surface 172 maintained against the upper locator surface 94, the contour of the upper locator surface 94 will determine the depth of the outline groove 190 at any particular location along the length of the guide slot 120, in accordance with the predetermined distance D between the radial bearing surface 172 and radial cutting surface 164 at the far end 162, thereby outlining a predetermined contour in the seating surface 46, as well as the area 49 of the seating surface 46. The diameter of the radial bearing surface 172 relative to the width 126 of the guide slot 120 assures that the radial bearing surface 172 bridges the width 126 of the guide slot 120 so as to overlie and be maintained against the upper locator surface 94 adjacent both the outer locator edge 122 and the inner edge 124 of the guide slot 120, thereby assuring stability as well as accurate location of the burr 156, and the cutting surfaces 158 and 164 thereof, during translation of the burr assembly 150 and cutting of the outline groove 190.

In the illustrated embodiment, as best seen in FIGS. 6 and 8, the upper locator surface 94 includes a first portion 192 adjacent the first leg 140 of the guide slot 120, and a second portion 194 adjacent the second leg 142. The first portion 192 is spaced altitudinally from the lower guide locating surface 96 of guide block 84 a first altitudinal distance 196, and the second portion 194 is spaced altitudinally from the lower guide locating surface 96 a second altitudinal distance 198 different from the first altitudinal distance 196. In this instance, where the guide block 84 is placed on the condyle 32 with the first leg 140 of the guide slot 120 located nearer to the trochlear groove 36 and the second leg 142 located further from the trochlear groove 36, first portion 192 of the upper locator surface 94 is nearer to the trochlear groove 36 and second portion 194 is further from the trochlear groove 36, and the first altitudinal distance 196 is less than the second altitudinal distance 198 so that the depth of the outline groove 190 is greater nearer to the trochlear groove 36 than the depth of the outline groove 190 further from the trochlear groove 36. For example, where the depth of outline groove 190 along the peripheral boundary 50 of seating surface 46 nearer to the trochlear groove 36 is about 4.5 mm, the depth of the outline groove 190 along the peripheral boundary 50 further from the trochlear groove 36 is about 3.5 mm. Thus, once the traverse of the burr assembly 150 along the guide slot 120 is complete, the combination of the guide block 84 and the burr assembly 150 assures that the outline groove 190 is properly placed on the condyle 32 and accurately delineates the area 49 of the seating surface 46 to be completed on the condyle 32, with the depth of outline groove 190 varied along the length of the outline groove 190 in accordance with the desired contour configuration of the seating surface 46.

Figure 13:
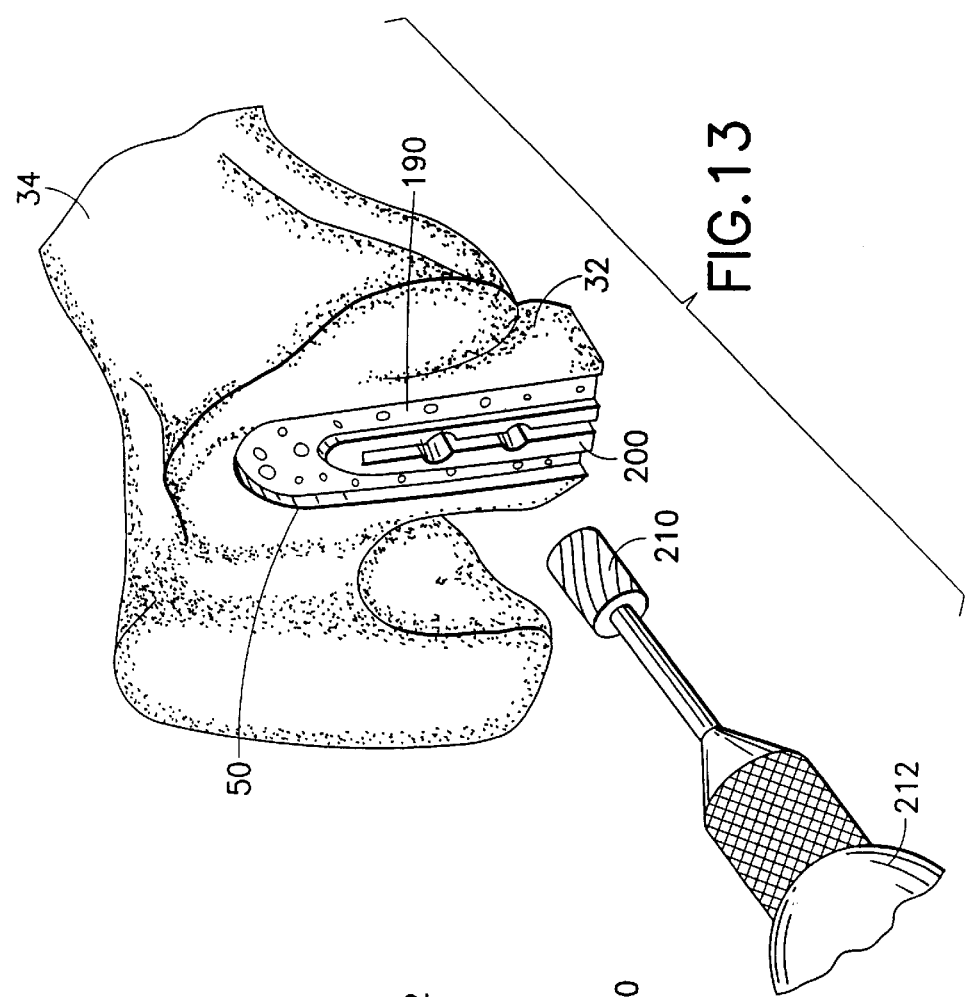
FIG. 13 is a pictorial perspective view showing the condyles subsequent to the procedure of FIGS. 11 and 12, and prior to a further cutting step of the method.

Turning now to FIG. 13, the guide block 84 has been removed from condyle 32, exposing the outline groove 190 and leaving behind an island 200 of bone which had been masked by central portion 103 of the guide block 84. The bone of island 200 then is removed with a removal tool, preferably in the form of a burr 210 rotated by a power-operated tool 212 guided by hand by the surgeon, using the outline groove 190 as a guide: to complete the preparation of seating surface 46 within the peripheral boundary 50 now accurately defined by the outline groove 190. At the same time, the varied depth of outline groove 190 serves to guide the surgeon in providing the seating surface 46 with the desired depth and contour configuration.

It has been the practice in previous procedures to merely outline the peripheral boundary of a seating surface to be constructed on a condyle, using a template and a marker, such as methylene blue, to mark the peripheral boundary on the bone of the condyle, and then guide a burr freehand within the marked boundary to construct the seating surface. Such freehand guiding of the burr, while providing the surgeon with some discretion and versatility in completing the desired seating surface, relies solely upon the skill of the surgeon in guiding a burr freehand to maintain accuracy in the peripheral boundary of the completed seating surface. The present invention, while still allowing a certain amount of discretion on the part of the surgeon in accommodating particular conditions encountered at an implant site, and still preserving ease in completing preparation of the seating surface 46, provides uncompromised accuracy in maintaining the peripheral boundary 50 of the seating surface 46, and the area 49 of the seating surface 46, as well as a convenient and effective guide for the depth and contour configuration of the completed seating surface 46.

The apparatus and procedure of the present invention enables the implant of femoral component 30 with the removal of only a minimal amount of bone from the condyle 32, thereby reducing to a minimum intrusion into the knee joint 24. Preparation of the required accurate seating surface 46 is accomplished with ease, the accuracy of the depth, contour configuration and area of seating surface 46 being assured by the close control of the cutting of outline groove 190 attained as a result of the configuration of cutting block 84 and the mating burr assembly 150. The ability to obtain a controlled outline groove 190 matching the peripheral boundary 50 of the seating surface 46, as opposed to freehand cutting to a marked line on the surface of the bone of the condyle 32, as has been done in the past, renders the present procedure highly advantageous. At the same time, the procedure requires only a relatively compact apparatus, compatible with the limited access available at the knee joint 24, and reducing the intrusion into the knee joint 24 by instruments necessary for completing the procedure. In this regard, it is noted that the ability to insert the burr assembly 150 into the guide slot 120 at any selected location along the length of the guide slot 120 provides the surgeon with convenience and versatility in manipulating the apparatus for maximum effectiveness with minimal invasiveness.

While the term "cutting" has been used herein to describe the mechanism by which bone is removed, and the apparatus includes a "cutter", "cutting device" and "cutting surfaces", it is to be understood that these terms are meant to include removal of bone by any one of a variety of mechanisms such as, for example, by abrading, sawing, shaving, slicing or the like accomplished by a variety of tools, any one of which is meant to fall within the term "cutting device", "cutter" or "cutting surface".

It will be seen that the present invention attains the several objects and advantages summarized above, namely: Requires removal of only a minimal amount of the natural bone at the joint, consistent with enabling stable and secure affixation of each component part of the prosthetic device; attains accuracy in the delineation of the area, depth and contour configuration of the prepared surfaces of the bone which will receive a component part of the prosthetic implant; enables such accuracy within the confines of the limited access available at the joint, with minimal disturbance of surrounding tissue in the vicinity of the joint; allows the use of a minimum number of instruments and steps of limited complexity in carrying out the procedure; provides the ability to use currently available instruments in connection with elements of the present apparatus and current techniques in connection with the steps of the present method for compatibility and widespread acceptance among surgeons; allows a certain amount of discretion on the part of the surgeon in accommodating particular conditions encountered at an implant site, while preserving ease and accuracy in completing preparation of the site for the implant.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. Apparatus for preparing a seating surface of prescribed depth, contour configuration and area delineated by a prescribed peripheral boundary extending along the bone of a natural joint at which a prosthetic device is to be implanted, the bone having been provided with at least a partially prepared site for locating and seating a component part of the prosthetic device at the seating surface, the apparatus comprising:

a depth, contouring and area guide block having longitudinally opposite first and second ends, laterally opposite first and second sides, an upper locator surface and a lower guide locating surface;

at least a portion of the upper locator surface having a profile contour configuration essentially matching a corresponding portion of the contour configuration of the seating surface;

a holding arrangement integral with the guide block for holding the guide block on the bone at the site with the guide block placed at a predetermined location and orientation relative to the bone;

a guide slot passing altitudinally through the guide block from the upper locator surface to the lower guide locating surface, the guide slot having a length, a laterally outer locator edge extending along a path geometrically similar to the peripheral boundary of the seating surface, a laterally inner edge and a lateral width between the outer locator edge and the inner edge; and a cutting device for reception within the guide slot, the cutting device having a cutting axis for extending altitudinally when the cutting device is received within the guide slot, an axial cutting surface for rotation about the cutting axis, the axial cutting surface having a near end and a far end, a radial cutting surface transverse to the axial cutting surface at the far end, a radial bearing surface located at a predetermined axial distance from the radial cutting surface, and an axial bearing surface located axially between the radial bearing surface and the near end of the axial cutting surface;

the axial cutting surface having a diameter less than the lateral width of the guide slot, the axial bearing surface having a diameter less than the lateral width of the guide slot, and the radial bearing surface having a diameter greater than the lateral width of the guide slot, the diameters of the axial cutting surface, the axial bearing surface and the radial bearing surface having relative dimensions such that upon reception of the cutting device within the guide slot, the cutting device is capable of insertion axially into the guide slot in an altitudinal direction at any selected location along the length of the guide slot, the axial bearing surface follows the contour configuration of the outer locator edge of the guide slot to locate the axial cutting surface along the peripheral boundary of the seating surface while the radial bearing surface follows the upper locator surface, with the radial bearing surface overlying the outer locator edge and the inner edge of the guide slot to stabilize and locate the radial cutting surface at the prescribed depth of the seating surface.

2. The apparatus of claim 1 wherein:

the guide slot includes a first leg extending longitudinally from the first end of the guide block toward the second end of the guide block, adjacent the first side of the guide block, and a second leg extending longitudinally from the first end toward the second end of the guide block, adjacent the second side of the guide block; and the upper locator surface includes a first portion adjacent the first leg and spaced altitudinally from the lower guide locating surface a first altitudinal distance such that engagement of the radial bearing surface with the first portion of the upper locator surface will locate the radial cutting surface in place for establishing a first predetermined depth along a corresponding first portion of the seating surface, and a second portion adjacent the second leg and spaced altitudinally from the lower guide locating surface a second altitudinal distance different from the first altitudinal distance such that engagement of the radial bearing surface with the second portion of the upper locator surface will locate the radial cutting, surface in place for establishing a second predetermined depth along a corresponding second portion of the seating surface.

3. The apparatus of claim 2 for use where the natural joint is a knee joint, the prosthetic device is a prosthetic knee joint, the component part is a unicondylar femoral component, and the bone at the site includes a trochlear groove and a femoral condyle, and wherein the guide block is to be placed at the site with the first portion of the upper locator surface nearer to the trochlear groove and the second portion of the upper locator surface further from the trochlear groove, the apparatus including an improvement wherein the first altitudinal distance is less than the second altitudinal distance.

4. The apparatus of claim 3 wherein the guide slot includes a third leg extending laterally from the first leg to the second leg adjacent the second end of the guide block.

5. The apparatus of claim 3 for use where the site includes an essentially planar posterior surface formed on the femoral condyle, the apparatus including an improvement wherein the lower guide locating surface includes an essentially planar surface portion extending in an altitudinal direction for engaging the posterior surface to locate and orient the guide block on the bone at the site.

6. The apparatus of claim 1 wherein:

the guide slot includes a first leg extending longitudinally from the first end of the guide block toward the second end of the guide block, adjacent the first side of the guide block, and a second leg extending longitudinally from the first end toward the second end, adjacent the second side of the guide block; and the holding arrangement includes a post placed laterally intermediate the first and second legs and projecting altitudinally downwardly from the lower guide locating surface.

7. The apparatus of claim 1 wherein:

the guide slot includes a first leg extending longitudinally from the first end of the guide block toward the second end of the guide block, adjacent the first side of the guide block, and a second leg extending longitudinally from the first end toward the second end, adjacent the second side of the guide block; and the holding arrangement includes a fin placed laterally intermediate the first and second legs, projecting altitudinally downwardly from the lower guide locating surface, and extending longitudinally between the first and second ends of the guide block.

8. The apparatus of claim 7 wherein the holding arrangement includes a post placed laterally intermediate the first and second legs and projecting altitudinally downwardly from the lower guide locating surface.

9. The apparatus of claim 1 wherein the diameter of the axial cutting surface is less than the diameter of the axial bearing surface, and the outer locator edge of the guide slot extends adjacent the peripheral boundary of the seating surface, outside the area of the seating surface.

10. The apparatus of claim 9 wherein the cutting surface comprises a cylindrical cutting surface, and the axial bearing surface comprises a cylindrical bearing surface coaxial with the cylindrical cutting surface.

11. An improvement in an apparatus for preparing a seating surface of prescribed depth, contour and area placed within a prescribed peripheral boundary extending along the bone of a natural joint at which a prosthetic device is to be implanted, the bone having been provided with at least a partially prepared site for locating and seating a component part of the prosthetic device at the seating surface, the apparatus including a depth, contouring and area guide for guiding a cutting device to be received within the guide, the cutting device having a cutting axis for extending altitudinally within the guide, an axial cutting surface for rotation about the cutting axis, the axial cutting surface having a first diameter, a near end and a far end, a radial cutting surface transverse to the axial cutting surface at the far end, a radial bearing surface having a second diameter and being located at a predetermined axial distance from the radial cutting surface, and an axial bearing surface having a third diameter and being located axially between the radial bearing surface and the near end of the axial cutting surface, the improvement comprising:

a depth, contouring and area guide block having longitudinally opposite first and second ends, laterally opposite first and second sides, an upper locator surface and a lower guide locating surface;

at least a portion of the upper locator surface having a profile contour configuration essentially matching a corresponding portion of the contour configuration of the seating surface;

a holding arrangement integral with the guide block for holding the guide block on the bone at the site with the guide block placed at a predetermined location and orientation relative to the bone; and a guide slot extending altitudinally through the guide block from the upper locator surface to the lower guide locating surface, the guide slot having a length, a laterally outer locator edge following a path geometrically similar to the peripheral boundary of the seating surface, a laterally inner edge and a lateral width between the outer locator edge and the inner edge;

the lateral width of the guide slot being greater than each of the first and third diameters and less than the second diameter with the first, second and third diameters having relative dimensions such that upon reception of the cutting device within the guide slot, the cutting device is capable of insertion axially into the guide slot in an altitudinal direction at any selected location along the length of the guide slot, the axial bearing surface follows the outer locator edge of the guide slot to locate the axial cutting surface along the peripheral boundary of the seating surface while the radial bearing surface follows the upper locator surface, with the radial bearing surface overlying the outer locator edge and the inner edge of the guide slot to stabilize and locate the radial cutting surface at the prescribed depth of the seating surface.

12. The improvement of claim 11 wherein:

the guide slot includes a first leg extending longitudinally from the first end of the guide block toward the second end of the guide block, adjacent the first side of the guide block, and a second leg extending longitudinally from the first end toward the second end of the guide block, adjacent the second side of the guide block; and the upper locator surface includes a first portion adjacent the first leg and spaced altitudinally from the lower guide locating surface a first altitudinal distance such that engagement of the radial bearing surface with the first portion of the upper locator surface will locate the radial cutting surface in place for establishing a first predetermined depth along a corresponding first portion of the seating surface, and a second portion adjacent the second leg and spaced altitudinally from the lower guide locating surface a second altitudinal distance different from the first altitudinal distance such that engagement of the radial bearing surface with the second portion of the upper locator surface will locate the radial cutting surface in place for establishing, a second predetermined depth along a corresponding second portion of the seating surface.

13. The improvement of claim 12 for use where the natural joint is a knee joint, the prosthetic device is a prosthetic knee joint, the component part is a unicondylar femoral component, the bone at the site includes a trochlear groove and a femoral condyle, and wherein the guide block is to be placed at the site with the first portion of the upper locator surface nearer to the trochlear groove and the second portion of the upper locator surface further from the trochlear groove, the improvement including a construction wherein the first altitudinal distance is less than the second altitudinal distance.

14. The improvement of claim 13 wherein the guide slot includes a third leg extending laterally from the first leg to the second leg adjacent the second end of the guide block.

15. The improvement of claim 13 for use where the site includes an essentially planar posterior surface formed on the femoral condyle, the improvement including a construction wherein the lower guide locating surface includes an essentially planar surface portion extending in an altitudinal direction for engaging the anterior surface to locate and orient the guide block on the bone at the site.

16. The improvement of claim 11 wherein:

the guide slot includes a first leg extending longitudinally from the first end of the guide block toward the second end of the guide block, adjacent the first side of the guide block, and a second leg extending longitudinally from the first end toward the second end, adjacent the second side of the guide block; and the holding arrangement includes a post placed laterally intermediate the first and second legs and projecting altitudinally downwardly from the lower guide locating surface.

17. The improvement of claim 11 wherein:

the guide slot includes a first leg extending longitudinally from the first end of the guide block toward the second end of the guide block, adjacent the first side of the guide block, and a second leg extending longitudinally from the first end toward the second end, adjacent the second side of the guide block; and the holding arrangement includes a fin placed laterally intermediate the first and second legs, projecting altitudinally downwardly from the lower guide locating surface, and extending longitudinally between the first and second ends of the guide block.

18. The improvement of claim 17 wherein the holding arrangement includes a post placed laterally intermediate the first and second legs and projecting altitudinally downwardly from the lower guide locating surface.

19. An improvement in an apparatus for preparing a seating surface of prescribed depth, contour and area delineated by a prescribed peripheral boundary extending along the bone of a natural joint at which a prosthetic device is to be implanted, the bone having been provided with at least a partially prepared site for locating and seating a component part of the prosthetic device at the seating surface, the apparatus including a depth, contouring and area guide block having longitudinally opposite first and second ends, laterally opposite first and second sides, an upper locator surface and a lower guide locating surface, at least a portion of the upper locator surface having a profile contour configuration essentially matching a corresponding portion of the contour configuration of the seating surface, a holding arrangement integral with the guide block for holding the guide block on the bone at the site with the guide block placed at a predetermined location and orientation relative to the bone, a guide slot extending altitudinally through the guide block from the upper locator surface to the lower guide locating surface, the guide slot having a length, a laterally outer locator edge following a path geometrically similar to the peripheral boundary of the seating surface, a laterally inner edge and a lateral width between the outer locator edge and the inner edge, the improvement comprising:

a cutting device for reception within the guide slot, the cutting device including a cutting axis for extending altitudinally when the cutting device is received within the guide slot;

an axial cutting surface for rotation about the cutting axis, the axial cutting surface having a near end and a far end;

a radial cutting surface transverse to the axial cutting surface at the far end;

a radial bearing surface located at a predetermined axial distance from the radial cutting surface; and an axial bearing surface located axially between the radial bearing surface and the near end of the axial cutting surface;

the axial cutting surface having a diameter less than the lateral width of the guide slot, the axial bearing surface having a diameter less than the lateral width of the guide slot, and the radial bearing surface having a diameter greater than the lateral width of the guide slot, the diameters of the axial cutting surface, the axial bearing surface and the radial bearing surface having relative dimensions such that upon reception of the cutting device within the guide slot, the cutting device is capable of insertion axially into the guide slot in an altitudinal direction at any selected location along the length of the guide slot, the axial bearing surface follows the outer locator edge of the guide slot to locate the axial cutting surface along the peripheral boundary of the seating surface while the radial bearing surface follows the upper locator surface, with the radial bearing surface overlying the outer locator edge and the inner edge of the guide slot to stabilize and locate the radial cutting surface at the prescribed depth of the seating surface.

20. The improvement of claim 19 wherein the diameter of the axial cutting surface is less than the diameter of the axial bearing surface, and the outer locator edge of the guide slot extends adjacent the peripheral boundary of the seating surface, outside the area of the seating surface.

21. The improvement of claim 20 wherein the cutting surface comprises a cylindrical cutting surface, and the axial bearing surface comprises a cylindrical bearing surface coaxial with the cylindrical cutting surface.

22. A method of preparing a seating surface of prescribed depth, contour and area delineated by a prescribed peripheral boundary extending along the bone of a natural joint at which a prosthetic device is to be implanted, the bone having been provided with at least a partially prepared site for locating and seating a component part of the prosthetic device at the seating surface, the method comprising the steps of:

positioning a depth, contouring and area guide on the bone at the site, the guide including a guide slot having a length following a path geometrically similar to the peripheral boundary of the seating surface, the length including longitudinal length portions spaced apart laterally;

engaging a cutting device with the guide by inserting the cutting device altitudinally through the guide slot at any selected location along the path of the guide slot;

translating the cutting device along the length of the guide slot to cut an outline groove in the bone coincident with the peripheral boundary of the seating surface such that the outline groove establishes an outline contiguous with the area of the seating surface;

removing the guide from the bone subsequent to translating the cutting device along the length of the guide slot; and removing portions of the bone lying within the area contiguous with and delineated by the outline groove to establish the seating surface.

23. The method of claim 22 including the step of varying the depth of the outline groove along the length of the outline groove to provide different groove depths at different locations along the length of the outline groove, in accordance with the contour of the seating surface.

24. The method of claim 23 for use where the natural joint is a knee joint, the prosthetic device is a prosthetic knee joint, the component part is a unicondylar femoral component, the bone at the site includes a trochlear groove and a femoral condyle, the method including an improvement wherein the step of varying the depth of the outline groove includes varying the depth of the outline groove from a greater depth nearer to the trochlear groove to a lesser depth further from the trochlear groove.

* * * * *

UNITED STATES PATENT AND TRADEMARK OFFICE
CERTIFICATE OF CORRECTION

PATENT NO. : 6,554,838 B2 Page 1 of 1
DATED : April 29, 2003
INVENTOR(S) : Michael J. McGovern et al.

It is certified that error appears in the above-identified patent and that said Letters Patent is hereby corrected as shown below:

Drawings,
Fig. 6, please change the lead line for reference character 124 to extend to the laterally inner edge of guide slot 120.

Signed and Sealed this

Twenty-seventh Day of July, 2004

JON W. DUDAS
*Acting Director of the United States Patent and Trademark Office*